United States Patent [19]

Moorehead

[11] 4,068,659

[45] Jan. 17, 1978

[54] CATHETER PLACEMENT ASSEMBLY

[75] Inventor: Harvey Robert Moorehead, Salt Lake City, Utah

[73] Assignee: Deseret Pharmaceutical Co., Inc., Sandy, Utah

[21] Appl. No.: 704,715

[22] Filed: July 12, 1976

[51] Int. Cl.² ............................................. A61M 5/00
[52] U.S. Cl. ......................... 128/214.4; 128/DIG. 16; 128/348
[58] Field of Search ...................... 128/214.4, 221, 348, 128/DIG. 16

[56] References Cited

U.S. PATENT DOCUMENTS

| 2,423,762 | 7/1947 | Everett | 128/215 |
| 3,000,380 | 9/1961 | Doherty | 128/214.4 |
| 3,010,453 | 11/1961 | Doherty | 128/214.4 |
| 3,185,152 | 5/1965 | Ring | 128/214.4 |
| 3,220,411 | 11/1965 | Czorny | 128/214.4 |
| 3,370,587 | 2/1968 | Vizcarra | 128/214.4 |
| 3,703,174 | 11/1972 | Smith | 128/214.4 |
| 3,792,703 | 2/1974 | Moorehead | 128/214.4 |

FOREIGN PATENT DOCUMENTS

| 1,064,445 | 12/1953 | France | 128/214.4 |

*Primary Examiner*—Dalton L. Truluck
*Attorney, Agent, or Firm*—Lynn G. Foster

[57] ABSTRACT

A disposable assembly and associated method for placing a catheter tube or plastic cannula into the body of a patient, the assembly being initially disposed in a sterile package and comprising a hollow cannulated needle sharpened at one end and comprising a connector in the form of a hub at the trailing end thereof, the connector being joined to an elongated semi-rigid sheath having a longitudinal slit along one location. The flexible cannula of radiopaque silicone rubber, is initially disposed within the semi-rigid sheath with the leading end thereof resting within the hollow of the needle. A stylet telescopically rests within the entire length of the plastic cannula with the exception of the leading tip thereof and is of such dimension as to stiffen the concentrically disposed plastic cannula. An inserter mechanism comprising a laterally projecting handle is connected to the trailing end of the stylet such that the handle thereof extends through the longitudinal slit in the semi-rigid sheath and is exposed for manual manipulation. The trailing end of the semi-rigid slitted sheath is plugged and/or capped to maintain sterility. In use, once the assembly has been removed from the sterile package and venipuncture has been accomplished, the catheter tube or plastic cannula is concurrently advanced into the vein with the stylet through manual manipulation of the inserter handle, so as to preserve the sterilizing of the catheter tube following which the plastic cannula is retained in the vein and, the remainder of the catheter placement assembly other than the plastic cannula is retracted rearwardly and entirely removed from the plastic cannula at the trailing end thereof and discarded. The relationship between the plastic cannula and the inserter precludes reverse displacement of the plastic cannula during insertion thereby obviating any possibility of shearing of the plastic cannula into the vein. Thereafter, a suitable plug receiving female adapter is retrieved from the sterile package and is affixed to the trailing end of the plastic cannula to accommodate fluid flow through the cannula, usually from a syringe or infusion system.

18 Claims, 7 Drawing Figures

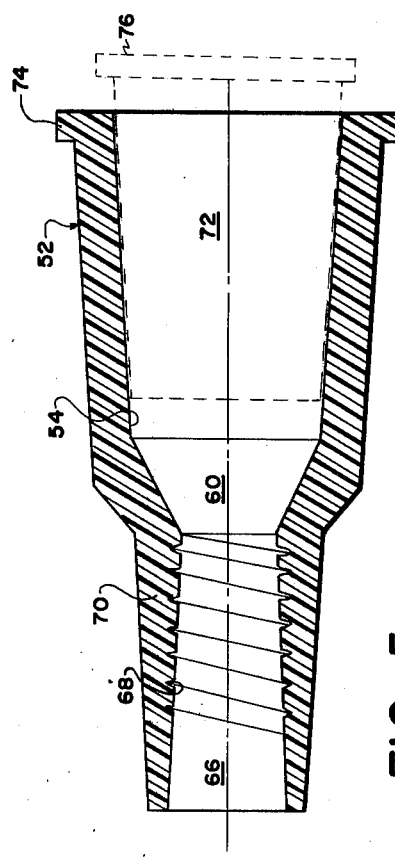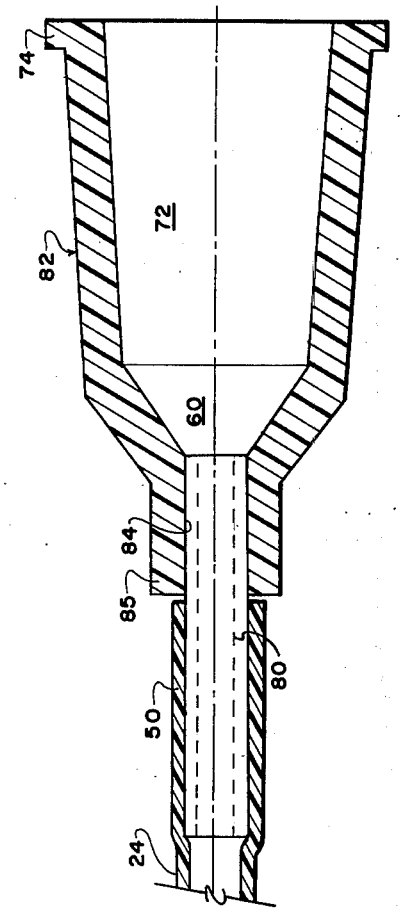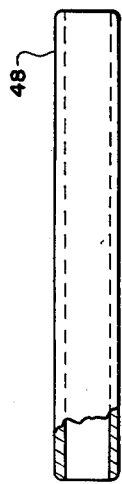

CATHETER PLACEMENT ASSEMBLY

BACKGROUND

Field of Invention

The present invention relates broadly to intravenous catheters to accommodate fluid flow into and out of body cavities of patients and more particularly to a novel inside-the-needle apparatus for and method of placement of a soft sterile plastic cannula or catheter tube into the vein of a patient.

Prior Art

Heretofore, various attempts to introduce a soft pliant cannula into the vein of a patient have been made. In some instances, a plastic cannula has been disposed on the outside of an insertion needle and the tube placed in the vein together. The needle is thereafter withdrawn leaving the catheter in the vein. However, the length of the plastic cannula that can be employed with this arrangement is limited to the length of the needle. In other instances, a plastic cannula has been telescopically inserted into the vein through the hollow of a needle following venipuncture. Thereafter, the needle is removed from the vein and the cannula retained therein to accommodate fluid flow. A certain amount of trauma and patient incompatibility and partial rejection have resulted when polyvinyl chloride, TEFLON (a registered trademark) or like stock tubing has been used to comprise the plastic cannula. Further, removal of the needle "from the arm" at the trailing end of the cannula has presented additional problems. Slotted needles have sometimes been employed, the slot being wide enough so that the needle may be laterally separated from around the cannula after being withdrawn from the vein. Split needles which can be separated into two pieces and thereby removed from the cannula have also been proposed. Unslotted needles have been used and allowed to remain "on the arm" surrounding that portion of the cannula exposed outside the vein. This has created a problem of either immobilizing the patient or protecting the needle so that the patient is not injured by the needle. Typically, a needle protector has been snapped or otherwise placed about the sharpened leading tip of such a needle and the protector or cover guard thereafter secured to the arm of the patient by adhesive or the like.

Another concern which has faced the medical profession in regard to the foregoing is the maintenance of sterility of the catheter after it is removed from its package and prior to placement and use in the arm of the patient.

In respect to inside-the-needle catheter placement units, a substantial amount of trauma and discomfort has been experienced by patients in the placement of the plastic cannula through the hollow of the needle following venipuncture. Attempts to use silicone rubber as the predominant material from which such a plastic cannula is formed have proved unacceptable because placement of such a highly flexible and pliant or limber plastic cannula has been extremely difficult and in many cases impossible, even though it is known that silicone rubber is far more compatible with the human body than polyvinyl chloride, TEFLON (a registered trademark) or the like.

From the foregoing, it should be appreciated that the two most dominant problems of concern are facile placement of a highly flexible plastic cannula of a silicone rubber or like material which is highly compatible with the human body appropriately in the vein without buckling, bending, or kinking so as to subsequently accommodate fluid flow therethrough at various and sundry times and removal from the arm of the needle and related paraphernalia of an inside-the-needle catheter placement unit following venipuncture.

BRIEF SUMMARY AND OBJECTS OF THE PRESENT INVENTION

With the foregoing in mind, the present invention is intended to overcome the above mentioned obstacles and to particularly provide a unique disposable catheter placement assembly comprising an inside-the-needle catheter tube or plastic cannula wherein all parts of the assembly other than the plastic cannula are removed "off the catheter tube" and "off the arm" after venipuncture and wherein a highly flexible plastic cannula having little if any body rigidity on its own may be facilely and reliably placed in the vein through the hollow of a needle following venipuncture in a relatively short period of time without buckling, bending or kinking wherein a much higher degree of patient compatability results and wherein any risk of shearing of the catheter tube is entirely avoided. It is of particular significance that the venipuncture and the placement of the plastic cannula in the vein occurs procedurally in such a fashion that human hand does not contact either component and, therefore, the initial sterility of the catheter tube is maintained, independent of whether or not the user of the catheter has engaged in sterilization procedures himself.

Accordingly, it a primary object of the present invention to provide novel methods and apparatus for placement of a plastic cannula in a body cavity of a patient.

A further paramount object of the present invention is the provision of apparatus for and methods of facilely and reliably inserting a highly pliant and extremely flexible plastic cannula of radiopaque silicone rubber into a body cavity, such as a vein, of a patient.

An additional primary object of the present invention is the provision of apparatus and methods whereby the cannulated needle and insertion structure for placement of a plastic cannula through the hollow of the needle may be entirely removed from the plastic cannula and discarded following venipuncture or the like.

A further important object of the present invention is the provision of an apparatus and method for inserting a highly pliant catheter through the hollow of a needle following venipuncture while maintaining sterility and accommodating complete removal of the needle and insertion paraphernalia from the catheter and the arm thereafter.

A further object of this invention is the provision for the insertion of a plastic cannula in the vein of the patient through the hollow of a needle in such a fashion as to prevent the operator or user from retracting the plastic cannula during insertion.

Another object of importance is the provision for stiffening and guiding of a highly limp plastic cannula during its insertion into the vein while preventing damage to the plastic cannula or to the patient.

Another object of the invention is to provide a catheter insertion mechanism which provides a visual indication of the length of the catheter tube introduced into the vein at any point in time.

Another object of the invention is to provide a soft pliable catheter tube having the trailing end stiffened to accommodate connection of the catheter tube to an intravenous infusion system.

Another object of the invention is to provide a catheter with a stiffened trailing end along with an initially separate connecting female adapter which is applied to the stiffened end of the catheter tube in sealed retained relationship to accommodate communication of fluid from an infusion system or the like.

Another object of the invention is to provide a separate female adapter for connecting to a stiffened trailing end of an indwelling soft pliable catheter tube, wherein the adapter deforms the trailing of the catheter tube to create the connection.

A further object is the provision of a novel apparatus for and method of placement of a catheter tube in the vein of a patient through the hollow of a needle which accommodates total separation of the needle and placement apparatus from the catheter tube prior to use.

An important object is the provision of a novel and safe catheter insertion mechanism comprising a slit sheath and a laterally exposed insertion handle.

These and other objects and features of the present invention will be apparent from the following detailed description taken with reference to the accompanying drawings.

BRIEF DESCRIPTION OF THE DRAWINGS

FIG. 4 is an elevational view of a hollow sleeve stiffener adapted to be placed within the hollow of the plastic cannula at the trailing end thereof;

FIG. 5 is a longitudinal cross sectional view of a plug receiving fluid infusion female adapter which may be connected to the stiffened trailing end of the catheter tube;

FIG. 6 is a longitudinal cross sectional view of the female adapter of FIG. 5 being twisted upon the stiffened trailing end of the catheter tube; and FIG. 7 is a longitudinal cross sectional view of a further female adapter embodiment adapted to be placed upon the unstiffened trailing end of the catheter tube following venipuncture and removal of the insertion mechanism and the needle from the catheter tube.

DETAILED DESCRIPTION OF THE ILLUSTRATED EMBODIMENT

Figure 1:
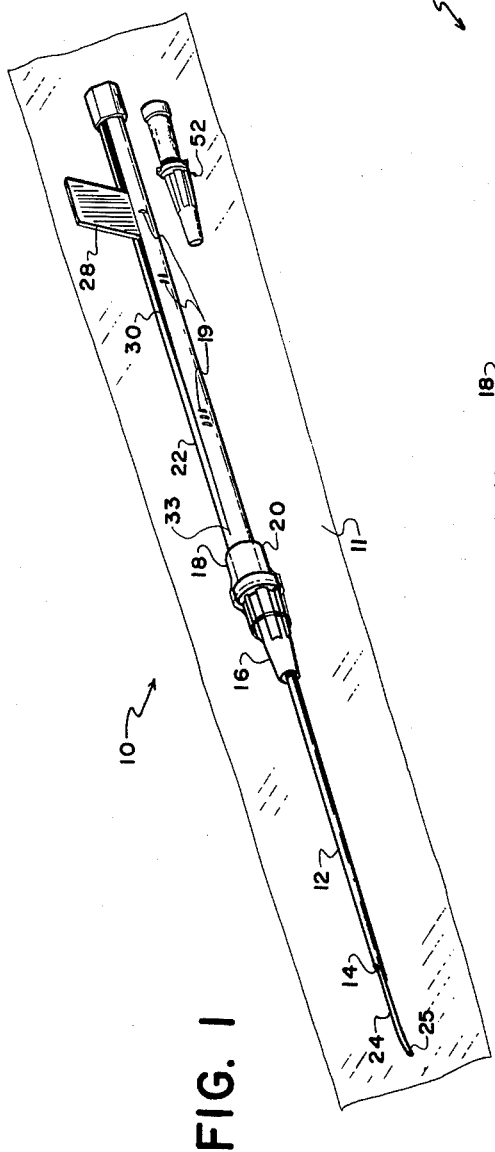
FIG. 1 is a perspective representation of a presently preferred catheter placement assembly contained within a sterile package, according to the present invention showing the catheter tube partially extended outside the needle.

Reference is now made to the drawings wherein like numerals are used to designate like parts throughout and which illustrate a presently preferred sterile disposable catheter placement assembly, generally designated 10, in accordance with the present invention for positioning a sterile catheter tube or plastic cannula into a body cavity of a patient, normally a vein of the cardiovascular system. FIG. 1 in particular illustrates the catheter placement assembly 10, which broadly comprises an inside-the-needle catheter placement assembly in its assembled condition, which assembly is preferably disposed in a sealed sterile package 11 following manufacture and prior to use. The package 11 also contains a female adapter 52 with a plug 76 therein for a purpose hereinafter explained.

The assembly 10 comprises a cannulated hollow metallic needle 12 which is sharpened at its leading end 14 and comprises a connector in the form of a female hub 16 at the trailing end. The hollow 17 of the connector 16 is in axial alignment with the hollow 13 of the needle 12. A sterile tubular sheath 22 of semi-rigid thin wall plastic material such as polyethylene is joined at its leading end 21 to the connector 16 by use of a sleeve 18 of heat shrinkable material. Naturally, any other mechanism other than hub 16 and sleeve 18 for connecting the trailing end of the needle to the leading end 21 of the sheath 22 so as to provide a continuous axial passageway of sufficient size would be suitable. Utilizing the sleeve 18, it is preferred that the interface between the interior of the sleeve 18 and the exterior of the leading end 21 of the sheath 22 at interface 23 receive a suitable adhesive or bonding agent to ensure proper adhesion.

The shell sheath 22 comprises a longitudinal slit 30 which commences at site 33 slightly rearward of the leading end 21 of the sheath 22 and extends along the remainder of the sheath 22. A plug 32 of suitable size is disposed within the trailing end of the tubular sheath 22 and a plastic cap 34 disposed about said trailing end. In this way the initial diameter of the tubular sheath 22 is accurately maintained so that the slit 30 is continuously urged into a closed, sterile disposition.

A catheter tube or plastic cannula 24 is initially disposed essentially entirely within the hollow of the sheath 22, the hollow 17 of the connector 16 and the hollow 13 of the needle 12, the leading end 25 of the plastic cannula 24 being initially disposed rearward of the sharpened tip 14 of the needle 12. The exact length of the catheter tube of plastic cannula 24 will naturally depend upon the combined lengths of the needle 12 and the sheath 22, each of which may be any one of several potential lengths. The diameter of the catheter is substantially constant and less than any and all of the diameters of the needle 12, the connector 16 and the sheath 22.

It is to be appreciated that the illustrated catheter tube 24 is of radiopaque silicone rubber, sometimes referred to as Silastic material, which is extremely pliable, limp and soft but highly compatible with human tissue creating little if any trauma or adverse reaction. Heretofore the "limp" nature of this particular material has made it impractical and undesirable to facilely and reliably place a catheter tube of this material in the vein of a patient using rapid placement venipuncture procedures similar to those in current use in hospitals. Accordingly, prior attempts to develop a commercially acceptable catheter placement assembly comprising a catheter tube of silicone rubber have failed. The present invention overcomes that negative legacy. Again, it is to be observed that the catheter tube 24 comprises a length of tubular silicone rubber stock unattached to any other part of the catheter placement assembly, the catheter tube being situated initially entirely within the hollow 13 of the needle, the hollow 17 of the female connector 16 and the hollow of the sheath 22.

Figure 2:
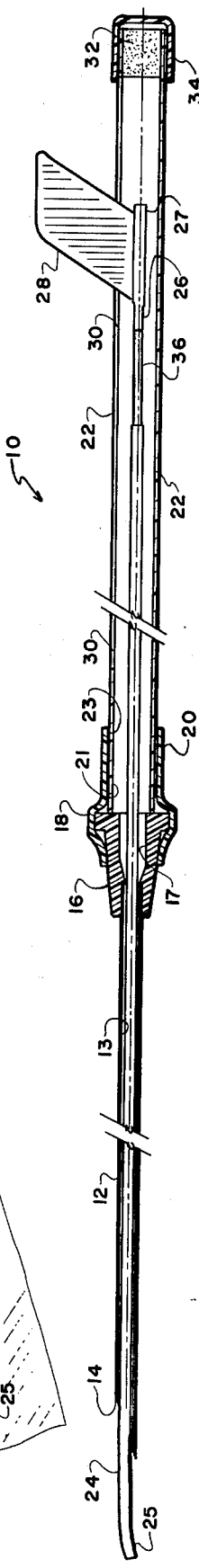
FIG. 2 is an enlarged longitudinal cross sectional representation of the catheter placement assembly of FIG. 1 again showing the catheter insertion mechanism and the catheter tube partially advanced beyond the leading end of the needle.
Figure 3:
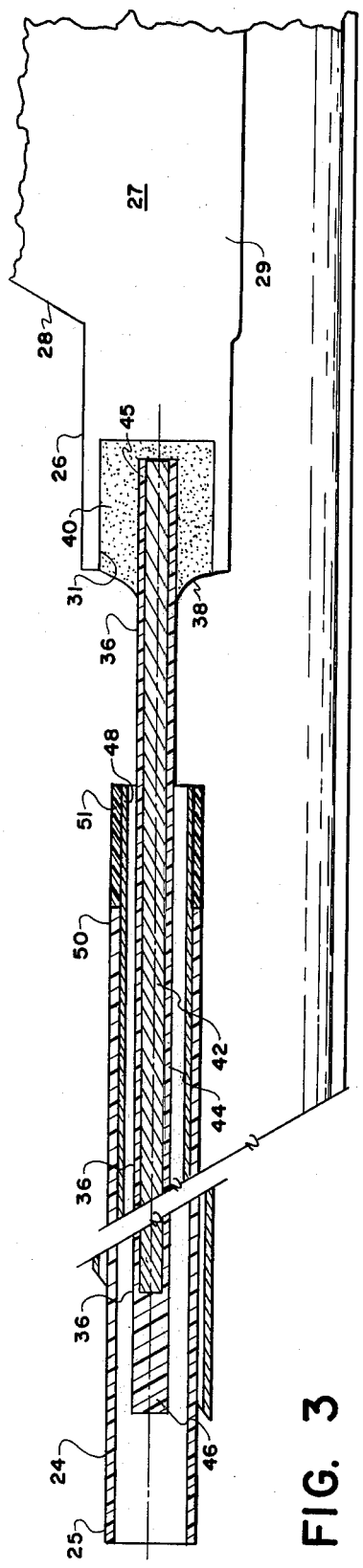
FIG. 3 is an enlarged fragmentary longitudinal cross sectional view of the trailing end of the plastic cannula or catheter tube and the insertion mechanism comprising a stiffening stylet, the trailing end of which loosely abuts to an inserter which comprises a laterally projecting handle to manually push the catheter tube into the vein following venipuncture the trailing end of the catheter tube being interiorly reinforced by a steel sleeve the end of which is covered by a TEFLON (a registered trademark) or like plastic sleeve.

As best seen in FIGS. 2 and 3, as part of an insertion mechanism, the stylet yieldable stiffener 36 extends through almost the entire length of the silicone rubber catheter tube 24, the leading end 46 of the stylet stiffener 36 terminating a short distance rearward of the distal end 25 of the catheter tube 24. While the stylet stiffener 36 may be any suitable flexible structure which will accommodate curvilinear flexing while preventing kinking, buckling and folding during insertion, the presently preferred and illustrated embodiment comprises a central resilient wire 42 of substantial rigidity, such as piano wire, and an exterior layer or coating of plastic 44, which prevents the wire 42 from doing any damage to the patient or the catheter tube 24. The exact outside diameter of the stiffening stylet may vary, depending upon the inside diameter of the catheter tube 24 and the amount of the stiffening desired for optimum intravenous placement of the tube 24. Not only does the stylet 36 stiffen the catheter tube, it provides an interior guide for the catheter tube during insertion. It is to be appreciated that the telescopic relation between the stiffener 36 and the catheter tube is an unattached relationship whereby the catheter tube does not follow the stiffener when the stiffener is retracted, for reasons hereinafter explained.

The trailing end 45 of the stylet 36 is anchored by epoxy or other suitable fastening material to an inserter 27. The inserter 27 is part of the overall insertion mechanism and comprises a generally cylindrical portion 29 which has a forward extension 26 and comprises an axially directed blind bore 31 into which the trailing end 45 of the stylet 36 is telescopically placed and bonded in said position by a suitable compound 40. The cylindrical inserter portion 29 is located entirely within the hollow interior of the sheath 22, rearward of the trailing end of the catheter tube 24, and loosely abuts the trailing end 45 of the catheter tube 24. The inserter 27 also comprises a laterally projecting handle 28 which is integral with the cylindrical portion 29 and projects from the interior of the sheath to the exterior thereof through slit 30, as best illustrated in FIG. 1.

Initially, the inserter mechansim comprising the stylet 36 and the inserter 27 with its laterally projecting handle 28 is disposed immediately adjacent the plug 32 and cap 34 closing the trailing end of the sheath 22. The insertion tab 28 is relatively thin or narow in its width so as to minimize the amount of spreading which occurs at the slit 30. The catheter tube 24, (which is concentrically disposed about but unattached to the stylet 36), the stylet 36 and the inserter 27 may be advanced in unison slideably following venipuncture, the sheath 22 and needle 12 serving as an outside guide for such advancement and the stylet 36 comprising a stiffener and an inside guide whereby the catheter tube 24 is appropriately advanced into the vein. This advancement preserves the sterility of the catheter tube 24 within the hollow of the needle 12 and the interior of the sheath 22 and is for the most part rectilinear, although the stylet 36 and catheter tube 24 are flexed during such advancement so as to readily conform to the shape and orientation of the vein in which placement is occurring. The amount of flexing accommodated by the stylet 36 is restricted so that no sharp curvature may occur and, therefore, no buckling, sharp bending or kinking results in the highly pliant silastic catheter tube 24. As the inserter 27 is advanced, the slit 30 is caused to open in front of the advancing tab and close behind the tab, the user gripping the tab 28 between his fingers for such manipulation.

It should be noted that during use, the catheter tube can only be displaced in the forward direction since it is not attached to the stylet or the inserter. In other words, if the catheter tube has been partially inserted into the vein and the stylet 36 and inserter 27 are retracted, the catheter tube is not similarly retracted. Accordingly, severance of the catheter tube 24 against the sharpened leading end 14 of the needle 12, which sometimes has been said to occur during such retraction, is entirely obviated. The present placement assembly and insertion mechanism are the first known development whereby silicone rubber, which is highly pliant and extremely biologically inert, may be facilely and reliably placed as a catheter tube in the vein of a patient. The high degree of softness and the limber nature of this particular material has made it heretofore impractical if not impossible to use such on a commercial basis in connection with rapid venipuncture techniques.

The stiffener 36 also functions to assure that the passage or hollow interior of the catheter of the plastic cannula 24 is not occluded during insertion.

Marks or indicia 19 on the side of the sheath provide a visual indication of the length of the catheter tube 24 which has been displaced into the vein at any point in time.

It is to be appreciated that one could eliminate much of the length of the stiffener 36 and utilize in lieu thereof a relatively short stylet which would be telescopically disposed only in the trailing end of the catheter tube 24 and thereby utilize the features of the present invention other than the silicone rubber catheter tube 24. In other words, catheter tubes comprised of polyvinyl chloride, CLEAREX (a registered trademark), TEFLON (a registered trademark) or like plastic material may be placed in the vein with or without a full length stylet stiffener using features of the present invention.

Venipuncture is typically accomplished by removing the assembly 10 from the package 11, gripping the assembly at connector 16 and forcing the needle tip 14 through the skin and subcutaneous tissue into the vein. Once venipuncture has occurred and the catheter tube 24 together with the stylet 36 and inserter 27 have been suitably advanced by manual manipulation of the handle 28 to place the catheter tube or plastic cannula 24 in a desired location within the vein (or other body cavity) of the patient, the entirety of the catheter placement assembly 10 (exclusive of the catheter tube 24) is removed from the catheter tube 24 and discarded. This is done by the user applying a measure of pressure to the skin over the vein and against the catheter tube 24 immediately adjacent the venipuncture site (if and to the extent necessary) and by withdrawing or retracting the needle 24 with its hub 16 together with the sheath 22, the stylet 36 and the inserter 27. As soon as said remainder of the catheter placement assembly (excluding the catheter tube 24) has cleared the trailing end of the catheter tube, it is preferably discarded as a unit, although separate removal of (A) the stylet and inserter, (b) the sheath (if the bond at sleeve 18 permits), and (c) the needle 12 and connector 18 could be resorted to.

At this point in time, it is requisite that the catheter tube 24, with the forward portion in the vein, be suitably equipped to accommodate fluid flow. For example, if fluid infusion into the vein is desired, the catheter tube 24 must be coupled to an intravenous infusion system. Any suitable type of coupling technique may be used.

One presently preferred inventive mechanism for coupling an infusion system to the catheter tube 24 is illustrated in FIGS. 3 through 6. Specifically, a metallic or other rigid tubular sleeve 48 (FIG. 4), preferably having a relatively thin wall, is press fit into the trailing end 50 of the catheter tube 24 as best illustrated in FIG. 3 in such a manner so as to not appreciably increase the outside diameter at the trailing end 50 of the catheter tube 24. If desired, the sleeve 48 may be bonded or otherwise secured in the indicated position. Thus, the trailing end 50 of the catheter tube 24 is stiffened and its outside diameter will remain essentially unchanged. Because of the softness of the silicone rubber of which catheter tube 24 is formed, it is sometimes desirable to leave the proximal portion of the steel sleeve 48 exposed and superimpose an adapter receiving plastic collar 51 thereover. Collar 51 may comprise CLEAREX (a registered trademark), polyvinyl chloride, TEFLON (a registered trademark) or the like and will present an outside diameter essentially the same as the outside diameter of the catheter tube at 50.

With the trailing end 50 of the catheter tube stiffened by steel sleeve 48 (with or without collar 51), a female adapter of rigid plastic material, generally designated 52, is threaded or twisted upon said trailing end to create a female hub at the trailing end of the catheter tube 24. The female adapter 52 comprises a hollow body which defines a throughbore 54 comprising a tapered rear plug-receiving portion 72 into which a conventional plug 76 may be fitted. The purpose of plug 76 is to prevent blood loss during periods of catheter nonuse and preferably has breather capability as is conventional to avoid air embolism. The throughbore 54 also comprises a more sharply inwardly tapered conical section 60 and a forward portion 66, which comprises a plurality of serrations 68. The taper at portion 66 allows the adapter 52 to be "started" upon the trailing end 50 of the catheter tube 24 or upon the collar 51, as the case may be.

The nature of the serrations or threads 68 may be of any suitable type, the object being that the inside diameter of the serrations or threads or at least some portion of the serrations or threads will be less than the initial outside diameter of the trailing end 50 of the catheter tube 24 or the collar 51, but in any event somewhat greater than the inside diameter of the catheter tube 24 at the end 50. Accordingly, as the adapter 54 and particularly the forward cylindrical projection 70 is caused to be twisted upon the trailing end 50 of the catheter tube 24 with one hand as the indwelling catheter tube is held by the other hand, the material of the end 50 (or at collar 51) is caused to be deformed into an exterior threaded configuration, as best illustrated in FIG. 6. As the twisted placement of the adapter occurs it is preferred that the hand securing the catheter tube also occlude the catheter tube by applying external pressure causing its temporary collapse.

Once the threading operation has been completed, the female adapter 52 will be secure on the trailing end 50 of the plastic cannula 24 (or on the collar 51). The adapter 52 comprises conventional luer dogs or lugs 74 which facilitate fluid flow through the catheter tube 24 either from an infusion system or a syringe. The deformed plastic at end 50 (or collar 51) creates a fluid seal and also is affixed to the adapter 52. The trailing end of the catheter tube and the adapter 52 are then taped to the arm.

An alternative approach for connecting the trailing end of the catheter tube to a syringe or an infusion system is illustrated in FIG. 7, which depicts a female adapter 82 similar in configuration at its trailing end to the femaleadapter 52 and thus comprising bore portions 72 and 60 as well as luer dogs 74. The cavity 72 may be appropriately plugged as indicated in FIG. 5. The leading end 85 of the adapter 82 comprises a cylindrical projection defining a central passage 84 in axial communication with the tapered passage 60. A hollow rigid sleeve is illustrated as being fitted within the hollow 84 of the projection 85 and is secured in that position by a suitable bonding material. A tube 80 may be similar or identical to the tube 48 of FIG. 4 or may comprise an integral part of the adapter 82 formed of plastic as one piece by molding or the like. The adapter 82 is placed by force fitting the rigid projecting tube 80 into the trailing end 50 of the catheter tube 24 as illustrated in FIG. 7 thereby creating a sealed retained relationship without appreciably increasing the outside diameter of end 50 of the catheter tube and defining a fluid passageway through the adapter 82 and the catheter tube 24.

It should further be appreciated that the sheath may be of transparent or translucent material so as to also define a flashback chamber.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A catheter placement assembly for displacing a catheter tube from a sterile sheath into a body cavity of a patient comprising:

a cannulated disposable needle having a sharpened leading end;

a substantially linear semi-rigid shape-retaining disposable sheath having an axial slit therein;

disposable hollow means connecting the trailing end of the needle to the leading end of the sheath whereby the needle, sheath and hollow means are joined together and discarded essentially simultaneously after use;

a flexible plastic catheter tube of substantially constant diameter throughout the entire length thereof at least the trailing end of which is initially disposed within the hollow of the sheath;

catheter advancing means comprising means abutting but separate from the trailing end of the catheter tube and manually manipulatable means connected to the abutting means and laterally projecting through said slit in the sheath whereby the catheter advancing means and the catheter tube are unitarily advanced and the catheter advancing means alone retracted for placement of the leading part of the catheter tube into the body cavity through the hollow of the needle following puncture, the catheter tube eventually becoming completely separated from the sheath and needle and the remainder of the assembly excluding the catheter tube being essentially unitarily discarded after said complete separation and while retaining the catheter tube within the body cavity.

2. A catheter placement assembly as defined in claim 1 wherein said hollow connecting means comprise a female needle hub.

3. A catheter placement assembly according the claim 1 further comprising means closing and sealing the trailing end of the hollow sheath.

4. A catheter placement assembly according to claim 1 further comprising a separate female adapter for connection to an infusion system, the separate female adapter comprising means for firmly affixing the adapter to the trailing end of the catheter tube following said separation of the remainder of the assembly from the catheter tube.

5. A catheter placement assembly according to claim 1 wherein the sheth comprises a tube of semi-rigid plastic material and said slit spans substantially all of the axial length of the sheath except the forward distal end.

6. A catheter placement assembly according to claim 1 further comprising markings on the sheath to indicate the depth of insertion of the catheter tube into the body cavity at any point in time.

7. A catheter placement assembly for displacing a catheter tube from a sterile sheath into a body cavity of a patient comprising:
a cannulated needle having a sharpened leading end;
a hollow semi-rigid sheath having an axial slit therein;
hollow means connecting the trailing end of the needle to the leading end of the sheath;
a flexible plastic catheter tube of substantially constant diameter at least the trailing end of which is disposed within the hollow of the sheath, the flexible plastic catheter tube comprising a material having the physical characteristics of silicone rubber;
catheter advancing means comprising means abutting the trailing end of the catheter tube and manually manipulatable means laterally projecting through said slit in the sheath whereby the catheter advancing means and catheter tube may be unitarily advanced and the catheter advancing means alone retracted for placement of the catheter tube into the body cavity through the hollow of the needle following puncture and accommodate complete separation of the remainder of the assembly from the catheter tube while retaining the catheter tube within the body cavity, the catheter advancing means comprise a stylet projecting forward from the abutting means telescopically within the cathether tube along substantially the entire length of the catheter tube.

8. A catheter placement assembly for displacing a catheter tube from a sterile sheath into a body cavity of a patient comprising:
a cannulated needle having a sharpened leading end;
a hollow shape-retaining sheath having an axial slit therein;
hollow means connecting the trailing end of the needle to the leading end of the sheath;
a flexible plastic catheter tube of substantially constant diameter throughout the entire length thereof at least the trailing end of which is not flared and is disposed initially in the hollow of the sheath;
catheter advancing means comprising means abutting substantially the entire trailing end of the catheter tube within the sheath, stylet means having a lateral dimension less than the abutting means and being connected to the abutting means and telescopically projecting into the hollow of the catheter tube at the trailing end of the catheter tube and manually manipulatable reciprocable means connected to the abutting means within the sheath and comprising tab means eccentrically projecting through said slit and being exposed outside the sheath to be gripped between the fingers of the user and axially advanced and retracted along said slit whereby the catheter advancing means and the catheter may be unitarily advanced and the catheter advancing means alone retracted along the slit for placement of the leading part of the catheter tube in the body cavity through the needle following puncture, the catheter tube eventually becoming completely separated from the sheath and needle and the remainder of the assembly excluding the catheter tube being essentially unitarily discarded while retaining the catheter tube within the body cavity.

9. A catheter placement assembly for displacing a catheter tube from a sterile sheath into the vein of a patient comprising:
a cannulated needle having a sharpened leading end;
a hollow semi-rigid sheath having an axial slit therein;
hollow means connecting the trailing end of the needle to the leading end of the sheath;
an unattached flexible catheter tube of substantially constant diameter comprising a material having the characteristics of silicone rubber, the trailing end of the catheter tube being disposed within the hollow of the sheath and the leading end within the hollow of the needle;
catheter advancement means comprising means abutting the trailing end of the catheter tube, stylet means connected to the abutting means and telescopically projecting into and along substantially the entire length of the catheter tube, and manually manipulatable means connecting to the abutment means within the sheath and laterally projecting through said slit in the sheath to be gripped between the fingers of the user whereby the catheter advancing means and the catheter tube may be unitarily advanced and the catheter advancing means alone retracted for placement of the catheter tube into the vein through the needle following venipuncture and accommodate complete separation of the remainder of the assembly from the catheter tube while retaining the catheter tube within the vein; and
a separate female adapter to be firmly affixed to the trailing end of the catheter tube following said separation of the remainder of the assembly from the catheter tube.

10. The catheter placement assembly of claim 9 wherein the trailing end of the catheter tube is interiorly reinforced and said separate female adapter comprises a body, passageway means through the body, means at the trailing end of the body for connection to a syringe or an infusion system, and a hollow projection at the forward end of the body, the hollow of the forward projection comprising threads the inside diameter of at least some of said threads being slightly less than the outside diameter of the trailing end of the catheter tube whereby the female adapter is firmly attached to the trailing end of the catheter tube by turning it upon the catheter tube to thereby create threads in the catheter tube and material at the trailing end thereof intermediate the threads within the hollow of the forward projection.

11. A catheter placement assembly according to claim 9 wherein said separate female adapter comprises a body, passageway means through the body, means at the trailing end of the body for connection to a syringe or an infusion system and a hollow projection at the forward end of the body, the exterior diameter of the hollow projection being somewhat greater than the interior diameter of the trailing end of the catheter tube whereby the projection may be firmly attached to the trailing end of the catheter tube by force fitting the same into the trailing end of the catheter tube.

12. A catheter placement assembly according to claim 9 wherein said catheter advancing means is solid throughout and provides no fluid flow pathway whatever.

13. A catheter placement assembly for displacing a catheter tube from a sterile sheath into the vein of a patient comprising:
a cannulated needle having a sharpened leading end;
a hollow semi-rigid sheath having an axial slit therein;
hollow means connecting the trailing end of the needle to the leading end of the sheath;
an unattached flexible catheter tube of substantially constant diameter comprising a material having the characteristics of silicone rubber, the trailing end of the catheter tube being disposed within the hollow of the sheath and the leading end within the hollow of the needle;
catheter advancement means comprising means abutting the trailing end of the catheter tube, stylet means connected to the abutting means and telescopically projecting into and along substantially the entire length of the catheter tube, and manually manipulatable means connecting to the abutment means within the sheath and laterally projecting through said slit in the sheath to be gripped between the fingers of the user whereby the catheter advancing means and the catheter tube may be unitarily advanced and the catheter advancing means alone retracted for placement of the catheter tube into the vein through the needle following venipuncture and accommodate complete separation of the remainder of the assembly from the catheter tube while retaining the catheter tube within the vein;
a separate female adapter to be firmly affixed to the trailing end of the catheter tube following said separation of the remainder of the assembly from the catheter tube; and
a sterile, destructable package in which the entire catheter placement assembly is initially disposed in sealed, sterile relation.

14. A catheter comprising:
a highly pliant elongated catheter tube the leading part of which is to be placed and left indwelling within the vein of a patient, the tube comprising silicone rubber and a radiopaque material therein and having a substantially constant outside diameter throughout the entire length of the catheter tube; and
hollow means on said catheter tube and located at the interior of the trailing end of the catheter tube which cannot be occluded, said interior means defining a constant, rigid inside surface at the interior of said trailing end for accommodating subsequent reception of a female adapter, said hollow means further having an outside surface no larger than said outside diameter of said catheter tube.

15. A catheter comprising:
a highly pliant elongated catheter tube the leading part of which is to be placed and left indwelling within the vein of a patient, the tube comprising silicone rubber and a radiopaque material therein and having a substantially constant outside diameter throughout the entire length of the catheter tube;
hollow means on said catheter tube and located at the interior of the trailing end of the tube which cannot be occluded, said interior means defining a constant, rigid inside surface and said hollow means further having an outside surface no larger than said outside diameter of said catheter tube; and
an initially separate hollow female adapter having means for manually causing the adapter to be secured to the trailing end of the catheter tube at least along the exterior of the catheter tube at said trailing end.

16. A catheter placement assembly comprising:
a highly pliant elongated tube of substantially uniform diameter throughout the entire length thereof to be placed and left indwelling within the vein of a patient, the tube consisting solely of radiopaque silicone rubber;
a hollow assembly for guided placement of the tube in the vein comprising:
a hollow needle having a sharpened leading tip telescopically receiving the leading portion of the tube therein;
a hollow longitudinally slit sheath connected to the needle in axial alignment therewith and telescopically receiving the trailing portion of the catheter tube therein;
an inserter mechanism comprising means loosely abutting the trailing end of the tube within the sheath whereby the tube is pushed into the vein following venipuncture, an extension attached to the abutting means projecting telescopically a substantial distance into the tube to stiffen the same and a handle connected to the abutting means and projecting laterally outward through the slit in the sheath to be manually held between the fingers of the user to advance the tube into the vein and to retract along and entirely remove the hollow assembly and the inserter mechanism from the tube.

17. A catheter comprising:
a highly pliant elongated tube of substantially uniform diameter throughout the length thereof to be placed and left indwelling within the vein of a patient through the hollow of a needle, the tube consisting solely of radiopaque silicone rubber;
relatively stiff sleeve means force fit into the trailing end of the tube with the trailing portion thereof exposed beyond the tube;
sleeve means of semi-flexible plastic material superimposed telescopically over the trailing end of the stiff sleeve means said semi-flexible sleeve means having an outside surface no larger than said outside diameter of said tube, and
a separate hollow female adapter having means for securing the adapter to the plastic sleeve means.

18. A method of placing a limber catheter tube in the vein of a patient, comprising the steps of:

provimg a limber catheter tube of substantially uniform diameter through the entire length thereof and no flare at the trailing end thereof, at least the trailing end of the catheter tube being initially disposed within the hollow of a shape-retaining sheath;

interiorly stiffening substantially the entire length of the catheter tube to avoid kinking and buckling but accommodating curvilinear flexing of the catheter tube;

guiding the catheter tube into the vein at a puncture site from the sheath and through the hollow of a needle having a sharpened leading tip and also through a hollow sleeve connecting the needle to the sheath the catheter tube being so displaced into the vein by manual manipulation of a tab laterally projecting through a slit in the sheath and abutting but being separate from the catheter tube;

essentially axially withdrawing the interior stiffening;

retracting and entirely removing and discarding the needle and all other items from the catheter tube;

attaching a plug receiving female adapter solely to the trailing end of the catheter tube for subsequent connection to a syringe or infusion system.

* * * * *